Figure 1:
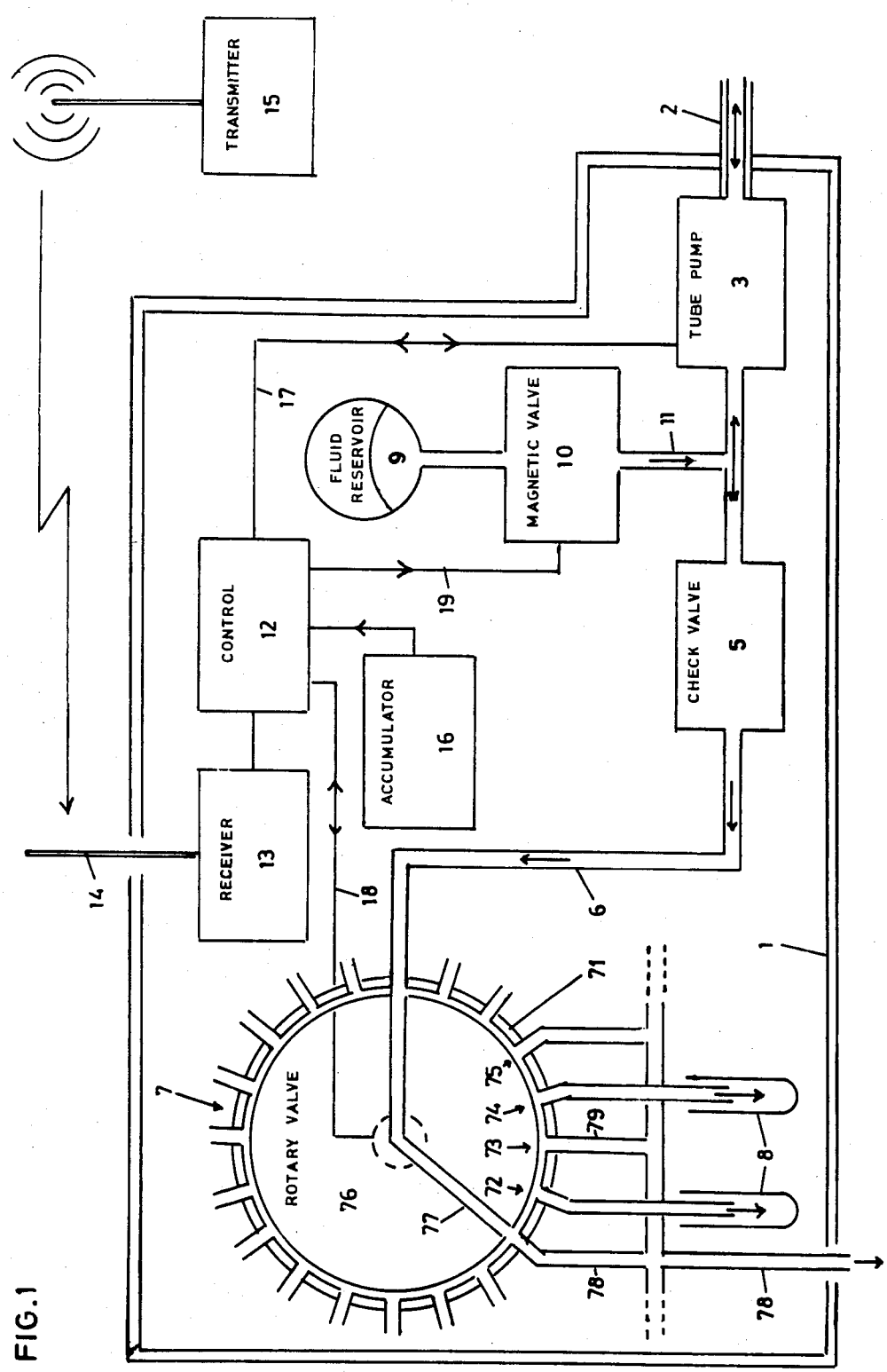

United States Patent [19]

Stephan

[11] Patent Number: 4,696,309

[45] Date of Patent: Sep. 29, 1987

[54] PORTABLE APPARATUS FOR TAKING BLOOD SAMPLES

[76] Inventor: Eberhart Stephan, Freihorstfeld 70, D-3000 Hannover 71, Fed. Rep. of Germany

[21] Appl. No.: 691,570

[22] PCT Filed: Apr. 5, 1984

[86] PCT No.: PCT/DE84/00078

§ 371 Date: Dec. 11, 1984

§ 102(e) Date: Dec. 11, 1984

[87] PCT Pub. No.: WO84/04033

PCT Pub. Date: Oct. 25, 1984

[30] Foreign Application Priority Data

Apr. 12, 1983 [DE] Fed. Rep. of Germany ....... 3313074

[51] Int. Cl.$^4$ ............................................... A61B 5/00
[52] U.S. Cl. ..................................... 128/762; 128/903
[58] Field of Search ............... 128/765, 766, 760, 762, 128/766, 750, 903, 637, 632, DIG. 3; 137/625.11; 251/129.04; 604/4, 122, 123, DIG. 3

[56] References Cited

U.S. PATENT DOCUMENTS

| 2,645,940 | 7/1953 | Kohl et al. | 251/129.04 |
| 3,513,845 | 5/1970 | Chesnut et al. | 604/4 |
| 3,570,314 | 3/1971 | Wagner | 137/625.11 |
| 3,995,494 | 12/1976 | Muller et al. | 137/625.11 |
| 4,008,717 | 2/1977 | Kowarski | 128/632 |
| 4,077,395 | 3/1978 | Woolner | 128/762 |
| 4,258,717 | 3/1981 | Bisera et al. | 128/637 |

Primary Examiner—Richard C. Pinkham
Assistant Examiner—Benjamin Layno
Attorney, Agent, or Firm—Robert E. Burns; Emmanuel J. Lobato

[57] ABSTRACT

Portable apparatus for repeatedly taking samples of blood or other body fluid from a person or animal comprises a housing adapted to be attached to the person or animal from which the samples are to be taken. The housing contains a pump having an inlet connected to a catheter inserted in the body of the person or animal and an outlet connected through a conduit and a multiple position first control valve to a storage receptacle having provision for separately storing a plurality of individual samples. A reservoir for rinsing fluid is connected through a second control valve to the conduit just downstream of the pump. A control system comprising a radio receiver for remote control controls the pump and second control valve to admit body fluid and rinsing fluid alternately to the conduit and controls the first control valve to direct individual samples of body fluid to the storage receptacle and to discharge rinsing fluid from the conduit. The storage receptacle comprises a plurality of small receptacles for individual samples or a continuous tube in which samples are spaced by gas.

10 Claims, 2 Drawing Figures

PORTABLE APPARATUS FOR TAKING BLOOD SAMPLES

The invention relates to portable apparatus for taking blood and other body fluids comprising a catheter, a pump and a storage container for the fluid taken.

The simplest known possibility for taking blood consists of a cylinder provided with a hollow needle on one end with a piston of which the piston rod extends out through the other end of the cylinder and ends in a ring through which the thumb of the hand is inserted with the fingers holding the cylinder during the taking of blood. Besides this simplest form of apparatus for taking blood, there are a variety of complicated forms of which the most expensive is mounted on a carriage.

With the direct blood extraction taken with these apparatuses, psychic influences act on the patient or other, for example physical, circumstances disturb the blood value and the blood extraction. It is true that with the more expensive types of these extraction apparatuses repeated blood extraction is possible, but however, these apparatuses are not portable by the patient.

In the field of medicine, information regarding the blood and its components and contents as well as with regard to physiological and pathological changes are of interest. This information can be obtained by taking blood tests and their analysis as well as through insertion of sensors and catheters. Through the direct taking of blood samples through puncturing, catheterization etc. the psychic influence of the patient can lead to an alteration of the blood value. Moreover, with many examinations under difficult conditions, for example running training, of rehabilitation patients, sportsmen, among others, and difficult examination of animals, such blood taking methods are possible only to a limited degree because the charge must be interrupted and the blood value can change in this time. With certain testing, for example simulated or actual flight situations with pilots and the examination of free-running animals among others, such examination is in general not possible.

For such examination of the blood and other body fluids under certain conditions on men and animals, there is required a portable blood taking apparatus which is freely selectable according to the situation or before a predetermined time of blood taking is so conducted that it is not necessary for a person to be present for the blood sampling.

The invention is directed to the problem of so constructing apparatus for taking body fluids of human and animal patients that the blood taking can be repeated at desired time intervals without requiring a person for servicing the blood taking apparatus to be present in the vicinity of the patient.

The portable extraction apparatus in accordance with the invention is characterized in that the control device (among others for the pump drive) can be switched on and, if desired, off by remote control, that for taking the body fluids there is provided a reservoir in which several body fluid samples can be stored, that there is provided a rinsing and filling arrangement for the pump, the catheter and the conduit system feeding from the pump to the reservoir, that there is provided a valve or valve system for conducting the body fluids taken and the rinsing and filling fluid for the canal system to the reservoir and that there is provided a control system for actuation of the rinsing and filling arrangement and the valve or valve system.

Such extraction apparatus can be housed in a housing with a safety belt. Through the remote control, which is advantageously a radio control, it is possible that either according to a preset program or according to the instructions of a person located at a distance, there can be transmitted to the extraction apparatus an impulse which controls the action of the pump drive and thereby leads to the taking of body fluid and finally the rinsing of the canal system of the apparatus and the pump as well as the catheter. It is a special advantage of this apparatus that the entire conduit system and the catheter are continuously filled with fluid and thereby free of gas. For the rinsing fluid is at the same time a filling fluid for the catheter. Instead of rinsing and filling fluid only filing fluid is referred to in the following description for the sake of simplicity. In the apparatus, a relatively large number of body fluid samples can be stored in storage receptacles. The components used lend themselves to extensive miniaturization. Moreover, this miniaturization leads to a very small energy source in the form of an electrical battery or an accumulator.

It is especially advantageous when the storage containers have several chambers for receiving samples, when in advance of the storage container there is arranged a multiple-way valve which for each position leads to a chamber for the reception of a sample and when in the multiple-way valve, there is provided a passage for the discharge of rinsing fluid. With this embodiment, the blood sampling can be constantly repeated, for example in the observation of the work process of a person or an animal without the patient being aware of and thereby influenced by it. In this manner the interference, for example on the influence of different organs on the blood before and during certain bodily and mental stress can be determined.

In this embodiment, it is advantageous when the multiple-way valve comprises a slider, preferably rotary slider, with a channel of which the discharge opening can be brought into communication with different inlet openings so that successively taken body fluids can be directed through different inlet openings to different storage chambers for the samples. However, one of these inlet openings does not lead to a storage chamber for a blood sample but serves as a free discharge for the rinsing fluid. Advantageously, alternate ones of these openings serve as a free discharge for the rinsing fluid.

The extracting apparatus can however have another form of storage container. An embodiment well suited for the desired miniaturization of the apparatus consists in that the storage container consists of a hose or tube in which samples of body fluid alternate with predetermined quantities of a separating gas (e.g. air or an inert gas) which after each actuation of the pump is introduced in the form of a bubble which separates individual samples from one another, that there is provided a supply container for the buffer gas, that a valve or a valve system is arranged ahead of the storage container with which, after each sample of body fluid, a predetermined amount of separating gas is introduced into the storage container and that a further valve or valve system is provided for the admission and discharge of a rinsing medium in the canal system between the pump and storage container on the one hand and the pump and the catheter on the other hand.

Switching technique simplifies the apparatus when the control device for the rinsing system together with its valve and/or the valve for the storage container are actuated by a pulse from the remote control and/or the pump.

Advantageously, the inlet for the rinsing fluid is arranged between the multiple-way valve and the pump. Thereby it can be advantageous when a check valve is arranged between the inlet for the rinsing fluid and the multiple-way valve.

Instead of the radio control, this operation can with a stationary operation, also be in another manner e.g. by a cable—e.g. with use of a large centrifuge—by a cable and sliding contact.

Through a built-in control device it is further possible to control further apparatus as desired e.g. recording or memory apparatus for physiological data or the like.

The advantages attainable with the invention exist especially therein that multiple body fluid extractions also under extremely difficult circumstances, are made possible without psychic stressing of the patient and without a further person in the close vicinity of the patient.

The taking of body fluid is carried out in the manner that the pump is set in operation for a predetermined time, that during a first time period the fluid drawn out by the pump is pumped in free discharge, that then the multiple-way valve is so positioned that the channel provided in the slider positioned before an inlet opening of a heretofore empty sample receiving chamber and that after a further predetermined time period the pump is deactivated in the manner that it remains in a flow-through permitting position and that the multiple-way valve is thereupon subsequently so positioned that the channel in the slider is aligned with the free discharge and that thereupon subsequently for a predetermined time, rinsing medium is supplied on the one hand to the multiple-way valve channel system and on the other hand to the tube pump and the catheter.

Figure 2:
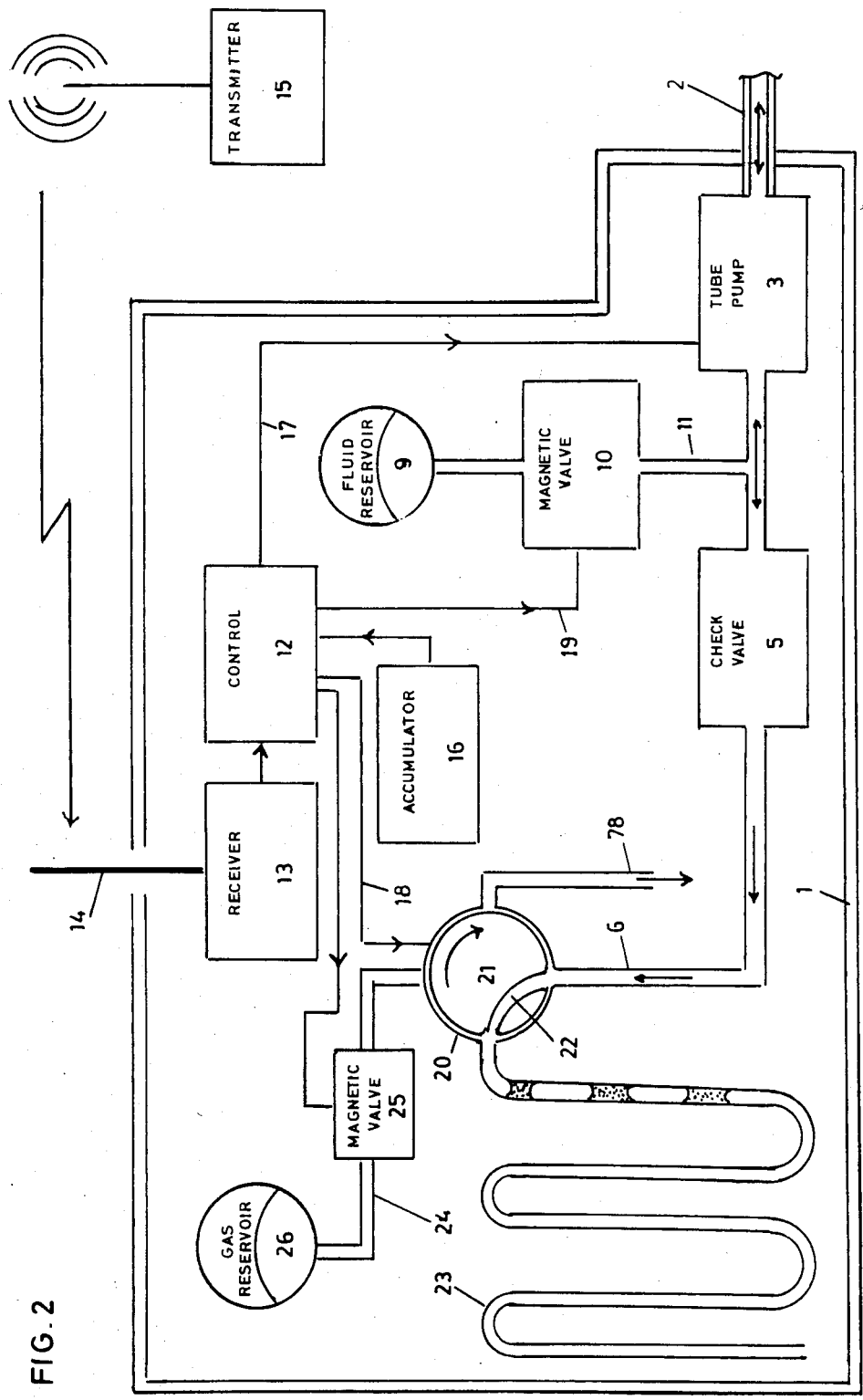

The essence of the invention is hereafter explained in more detail with the aid of two exemplified embodiments illustrated schematically in the drawing. It shows:

FIG. 1—an extraction apparatus with a storage receptacle having many individual chambers for the reception of the samples, FIG. 2—an extraction apparatus with a tube-form storage place.

The extraction apparatus is housed in a housing 1 which has a passage or connection nipple 2 for the entry or the connection of a permanent catheter. Body fluid drawn out of this permanent catheter through the connection nipple 2 by the tube pump 3 and conveyed through the channel 4, check valve 5 and channel 6 to a multiple-way valve 7, which in its housing 71 has a plurality of discharge openings 72, 73, 74, 75 . . . of which each second opening 72, 74 leads to separate receptacles 8 e.g. test tubes for the reception of body fluid samples while each intervening opening 73, 75 . . . leads to a common free discharge. In the multiple-way valve 7 there is arranged a slider 76 in which is provided a channel 77 that can connect channel 6 with one of the outlet openings 72, 73, 74, 75 . . . respectively. Advantageously, the slider 7 is a rotary slider with a central inlet and a peripheral outlet which communicates respectively with one of the discharge openings according to the valve position. At least one of the discharge openings in the housing 71 leads to the channel 78 for the free discharge of the rinsing fluid and for the discharge rinsing fluid - body fluid mixtures which are drawn in during the initial time of the tube pump and are conveyed through the channel system 4, 6 to the multiple-way valve.

For the rinsing after each individual body fluid extraction, there is provided a reservoir 9 from which a conduit 11 leads through a magnetic valve 10 to the channel 4. The reservoir 9 is advantageously a storage container formed as a gas-respectively air free flexible receptacle which collapses with the fractional extraction of the rinsing- and filling fluid. It is thereby assured that the entire catheter - tube system remains gas- and respectively air free. The extraction of the rinsing fluid takes place after opening of the magnetic valve over the line 19 through the action of the pump 3. For blood extraction a heparinized physiological cooking salt solution is used. The magnetic valve 10 and the multiple-way valve 7 as well as the pump 3 are activated through a control device 12. The action of this control device 12 is effected through a receiver 13 of which the antenna 14 receives signals from a transmitter 15. The electrical supply for the receiver 13, the control device 12, the magnetic valve 10 and the tube pump 3 takes place from an accumulator 16.

The control device 12 is put into operation through an impulse from the receiver 13 and releases the extraction procedure and the subsequent rinsing procedure in separate individual steps in the following manner: after impulses have been received to put the control device 12 into operation, the tube pump 3 is put into operation over the electric line 17 with the magnetic valve 10 closed. Thereby fluid from the permanent catheter 2 is introduced in the conduit 4, through the check valve 5 in the conduit 6 and from there into the multiple-way valve 7. This stands in such position that the channel 77 in the slider 76 opens into the discharge opening in the free discharge 78. Thereby the rinsing solution in the permanent catheter before the extraction as well as a part of the body fluid drawn out is conducted in free discharge (discarded). After a predetermined time period, a further electrical pulse is transmitted from the control device 12 over the electrical line 18 to the motor of the multiple-way valve 7 whereby its slider 76 is turned and indeed so that the channel 77 in the rotary slider 76 stops before the first discharge opening leading to a receiving chamber for the sample. Before each movement of the slider, the pump is stopped and is again put in operation when the slider reaches a new position. During each movement the rotary valve is free of pressure. The sealing surfaces are not loaded. If so much time has expired that the receiving chamber 8 for receiving the body fluid can be sufficiently filled, the control device 12 emits a further impulse which is conducted over the line 18 to the motor of the multiple-way valve so that this is advanced to the discharge opening 73 which is connected by the channel 79 with the conduit for free discharge 78 of the rinsing fluid. Further, this impulse is conducted through the line 17 to the tube pump and stops the pump. Further, this pulse acts over the line 19 on the magnet valve 10 which is opened for a short time and supplies rinsing and filling fluid over the conduit 11 to the channel 4, the check valve 5 and the multiple-way valve 7 and at the same time supplies rinsing fluid to the tube pump and the permanent catheter. After a predetermined short time period, the magnet valve is again closed and the apparatus is ready for the next extraction procedure. The exact position of the rotary slider is controlled by a light barrier. Upon the next extraction procedure, the rotary slider is so stopped with its channel 77 before the discharge opening that rinsing fluid present in the permanent catheter flows through the conduit 79 to the conduit 78 and can thereby be freely discharged. In this extraction procedure the rotary slider 77 is then turned so that its channel 77 is moved to the discharge opening 74 in order to fill the next storage chamber 8, which is connected to this discharge opening. Thus by each extraction of body fluid, another storage chamber 8 is filled. The motor of the multiple-way valve can be a stepping motor because between every three channels which lead to two adjacent room 8 there is arranged a channel which leads to the channel 78 for the free discharge of the rinsing fluid.

The embodiment of FIG. 2 differs essentially in that instead of the multiple-way valve 7 of FIG. 1 there is provided a three-way valve 20 of which the rotary slider 21 has a short curved channel 22. Further, instead of the different sample receiving chambers 8, there is a storage container in the form of a tube 23. The channel 22 connects in a first step of the extraction procedure the channel 6 with the free discharge conduit 78, in a second position by a second step, the channel 6 with the tube 23 and in a third step, the tube 23 through channel 24 and the magnetic valve 25 with the storage container 26 for the buffer gas. This storage container is a pressure container in which the separating gas is under high pressure.

The control of this extraction apparatus is effected in quite similar manner to the control of FIG. 1. Through a stepping switch a predetermined time after starting the apparatus, the rotary slider 21 is turned from the position in which the channel 22 connects the channel 6 with the discharge opening 78 to that position in which the channel 6 is connected with the tube 23. After a further time period through the stepping switch, the rotary slider 21 is further turned through 90° so that the channel 22 connects the supply 26 for the separating gas with the tube 23. The magnetic valve 25 is opened for a short time so that a predetermined amount of buffer gas can flow into the tube 23. Subsequently, there follow two switch steps, one after an another so that the rotary slider 21 is turned twice 90° whereby the channel 22 in the rotary slider 21 again connects the channel 6 with the discharge conduit 78. Now the rinsing with the rinsing fluid out of the reservoir can take place.

I claim:

1. Portable extraction apparatus of a size to be worn on the body for sequentially taking samples of blood and other body fluids comprising a housing containing:
    pump means having an outlet and an inlet, and first conduit means for connecting said inlet of said pump means to a catheter,
    multiple storage means providing a plurality of chambers for separately storing a plurality of samples of body fluid,
    fluid discharge means comprising a common discharge passage for discharging fluid not to be stored,
    first valve means having an outlet connectable alternatively to said storage means and said fluid discharge means and an inlet,
    second conduit means connecting the outlet of said pump with the inlet of said first valve means,
    a check valve in said second conduit means downstream of said pump to restrict flow of fluid in said second conduit means to flow in a direction from said pump to said first valve means,
    fluid reservoir means for storing a supply of rinsing fluid,
    third conduit means connecting said rinsing fluid reservoir means to a junction with said second conduit means at a location between said pump and said check valve,
    second valve means in said third conduit means for opening and closing said third conduit means, and,
    central control means for controlling said pump, said first valve means and said second valve means in accordance with the following program to:
    (a) operate said pump with said second valve means closed and said first valve means connecting the outlet thereof with said fluid discharge means to pump rinsing fluid and an initial portion of body fluid from said catheter to said fluid discharge means,
    (b) stop said pump and shift said first valve means to connect the outlet thereof with a chamber of said multiple storage means,
    (c) operate said pump to pump a sample of body fluid from said catheter to said chamber of said multiple storage means
    (d) stop said pump and shift said first valve means to connect the outlet thereof to said fluid discharge means,
    (e) open said second valve means for a short period of time to supply rinsing fluid through said third conduit means to said second conduit means, check valve and first valve means and to said pump and said first conduit means, and
    (f) close said second valve means and repeat said program with said outlet of said first valve means connected to a different chamber of said multiple storage means.

2. Portable extraction apparatus according to claim 1, in which said pump, first valve means and second valve means are electrically operated and are controlled by electrical signals from said central control means.

3. Portable extraction apparatus according to claim 2, in which said central control means comprises a radio receiver for receiving radio control signals from a remote radio transmitter.

4. Portable extraction apparatus according to claim 1, in which said multiple storage means comprises a plurality of sample receptacles and in which said first valve means comprises a stator having a plurality of ports of which alternate ports are connected with individual sample receptacles respectively and intervening ports are connected to said fluid discharge means and a slider operable to connect said conduit means successively with ports of said stator.

5. Portable extraction apparatus according to claim 4, in which said ports of said stator are arranged in a circle and said slider is rotatable.

6. Portable extraction apparatus according to claim 5, in which said slider is rotated by a stepping motor.

7. Portable extraction apparatus according to 1, in which said rinsing fluid reservoir means comprises an air-free flexible receptacle which collapses with the extraction of said rinsing fluid to assure that the entire system comprising said catheter, pump and first, second and third conduit means remains air free.

8. Portable extraction apparatus according to claim 1, in which there is provided a source of pressure gas and in which said multiple storage means comprises a continuous storage tube and said first valve means comprises means for admitting body fluid samples from said second conduit means and gas from said source alternately to said storage tube, whereby individual body fluid samples in said storage tube are separated from one another by gas.

9. Portable extraction apparatus according to claim 8, in which said first valve means comprises a stator having a first port communicating with said second conduit means, a second port communicating with said storage tube, a third port communicating with said source of pressure gas and a fourth port communicating with said fluid discharge means and a slider for sequentially connecting said first port with said second port, said second port with said third port and said fourth port with said first port.

10. Portable extraction apparatus according to claim 9, in which said ports of said stator are disposed in a circle and said slider is rotatable.

* * * * *